United States Patent [19]

Musser

[11] Patent Number: 4,870,210
[45] Date of Patent: Sep. 26, 1989

[54] AMINOGUANIDINE DERIVATIVE AS ANTI-INFLAMMATORY AGENTS

[75] Inventor: John H. Musser, Malvern, Pa.

[73] Assignee: American Home Products Corporation, New York, N.Y.

[21] Appl. No.: 134,672

[22] Filed: Dec. 18, 1987

[51] Int. Cl.$^4$ ............................................. C07C 133/10
[52] U.S. Cl. ..................... 564/228; 564/166; 564/168; 564/172; 564/180; 564/439; 560/34; 514/632; 514/311; 546/176
[58] Field of Search ............... 564/228, 168, 166, 177, 564/180, 108, 172; 514/632; 562/439; 560/34

[56] References Cited

U.S. PATENT DOCUMENTS

| | | | |
|---|---|---|---|
| 4,107,326 | 8/1978 | Goldman et al. | 564/228 |
| 4,139,555 | 2/1979 | Zeibes | 564/228 |
| 4,579,947 | 4/1986 | Devlin et al. | 544/400 |
| 4,665,085 | 3/1987 | Coquelet et al. | 564/228 |
| 4,705,782 | 11/1987 | Logan et al. | 564/228 |

FOREIGN PATENT DOCUMENTS

| | | | |
|---|---|---|---|
| 1187900 | 5/1985 | Canada | 564/228 |
| 188333 | 9/1986 | European Pat. Off. | |
| 1165013 | 3/1904 | Fed. Rep. of Germany | 564/228 |

*Primary Examiner*—James H. Reamer
*Attorney, Agent, or Firm*—George Tarnowski

[57] ABSTRACT

There are disclosed compounds of the formula

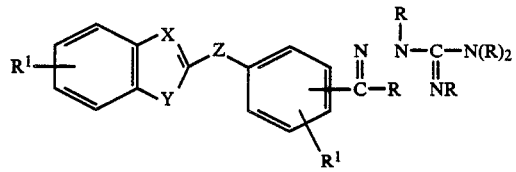

wherein

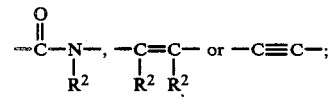

$$Y \text{ is } -O-, -S-, =N-, -\overset{R^2}{\underset{}{C}}=\overset{R^2}{\underset{}{C}}-, -N=\overset{R^2}{\underset{}{C}}- \text{ or } -\overset{R^2}{\underset{}{C}}=N-;$$

$$Z \text{ is } -CH_2O-, -CH_2S-, -CH_2N-, -O-, -S-, -N-, \\ \phantom{Z \text{ is } -CH_2O-, -CH_2S-,} R^2 \phantom{-O-, -S-,} R^2$$

$$-\overset{O}{\overset{\|}{C}}-N-, -\overset{R^2}{\underset{}{C}}=\overset{R^2}{\underset{}{C}}- \text{ or } -C\equiv C-; \\ \phantom{-C-}R^2$$

R is hydrogen, lower alkyl, phenyl or benzyl;
$R^1$ is hydrogen, lower alkyl, trifluoromethyl, amino, mono- or di- lower alkylamino, nitro, hydroxy, carboxy, lower alkoxycarbonyl, lower alkoxy or halo;
$R^2$ is hydrogen or lower alkyl;
and the pharmaceutically acceptable salts thereof, and their use in the treatment of psoriasis, ulcerative colitis, rheumatoid arthritis as well as in other inflammatory conditions.

2 Claims, No Drawings

AMINOGUANIDINE DERIVATIVE AS ANTI-INFLAMMATORY AGENTS

This invention relates to novel aminoguanidine derivatives possessing 5-lipoxygenase/cyclooxygenase inhibitory activity, which are useful as anti-inflammatory agents.

It is known that arachiodonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now know that prostaglandins arise from the endoperoxides $PGG_2$ and $PGH_2$ by the cyclooxygenase pathway of arachidonic acid metabolism. Other products arising from the endoperoxides in the cyclooxygenase patheway are prostacyclin ($PGI_2$) and the thromboxanes $(Tx)A_2$ and $B_2$. In the normal situation, the vasoconstrictive and platelet aggregating properties of the thromboxanes are balanced by $PGI_2$. There is now considerable evidence that of the various prostaglandin products of cyclooxygenase metabolism of arachiodonic acid, $PGE_2$ plays a major role in the development of inflammatory erythema, edema and pain. It is also known that $PGI_2$ also contributes to these responses. The role of $PGE_2$ in the development of erythema and enhancement of edema explains why cyclooxygenase inhibitors effectively reduce the redness and swelling associated with most inflammatory conditions [Ferreira and Vane, *Handb. Exp. Pharmacol.*, 50/II, 348–98 (1979)]. $PGE_2$ and $PGI_2$ are also involved in the pain of the inflammatory process; both induce hyperalgesia—sensitization of pain receptors through an edematous reaction or by direct effect—which results in potentiating the pain-producing effects of histamine or bradykinin. The inhibitors of cyclooxygenase, by removing the hyperalgesic cyclooxygenase products, function as analgesics.

In man, cyclooxygenase products have been detected in a number of inflammatory states, including allergic contact eczema, uveitis, arthritis, ulcerative colitis and psoriasis [Higgs et al., in Huskisson, E. C. ed., *Antirheumatic Drugs*, pp. 11-36, Praeger, Londong, 1983]. Clearly, drugs which exert an effect on the cyclooxygenase pathway of arachiodonic acid metabolism are considered to be useful in the treatment of inflammation and inflammatory conditions.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$, $D_4$ and $E_4$. The substance denominated slow-reacting substance of anaphylaxis (SRS-A) has been shown to consist of a mixture of sulfidopeptide leukotrienes, $C_4$, $D_4$ and $E_4$ [see Bach et al., *J. Immun.*, 215, 115-118 (1980); *Biochem. Biophys. Res. Commun.*, 93, 1121-1126(1980)].

The significance of these leukotrienes is that a great deal of evidence has been accumulated showing that leukotrienes participate in inflammatory reactions, exhibit chemotactic activities, stimulate lysosomal enzyme release and act as important factors in the immediately hypersensitivity reaction. It has been shown that $LTC_4$ and $LTD_4$ are potent bronchoconstrictors of the human bronchi [see Dahlen et al., *nature*, 288, 484-486 (1980) and Piper, *Int. Arch. Appl. Immunol.*, 76, suppl. 1, 43 (1985)] which stimulate the release of mucus from airways in vitro [Marom et al., *Am. Rev. Resp. Dis.*, 126, 449 (1982)], are potent vasodilators in skin [see Bisgaard et al, *Prostaglandins*, 23, 797 (1982)], and produce a weal and flare response [Camp et al., *Br. J. Pharmacol.*, 80, 497 (1983)]. The nonpeptide leukotriene, $LTB_4$, is a powerful chemotactic factor for leukocytes [see A. W. Ford-Hutchinson, *J. Roy. Soc. Med.*, 74, 831-833 (1981)], which stimulates cell accmulation and affects vascular smooth muscle [see Bray, *Br. Med. Bull.*, 39, 249 (1983)]. The activity of leukotrienes as mediators of inflammation and hypersensitivity is extensively reviewed in Bailey and Casey, *Ann. Reports Med. Chem.*, 17, 203-217 (1982).

Polymorphonuclear leukocytes (PMN's) are a major source of AA metabolites in the early stages of inflammation and drugs that inhibit leukocyte accumulation in inflamed tissues reduce the concentration of cyclooxygenase products in inflammatory exudates. Cyclooxygenase activity in inflammation may be suppressed through an effect on leukocyte migration. Thus, the suppression of leukocyte migration, which is enhanced by lipoxygenase oxidation products, also contributes to control of the inflammation process.

Accordingly, it is clear that in general inflammatory responses, where PG's are important mediators, dual inhibitors of cyclooxygenase and lipoxygenase must be considered the most useful therapeutic agents.

It has now been found that certain novel aminoguanidine derivatives inhibit and/or antagonize products of the cyclooxygenase and lipoxygenase pathways, and so are useful as anti-inflammatory agents. The present invention provides novel compounds having the following formula:

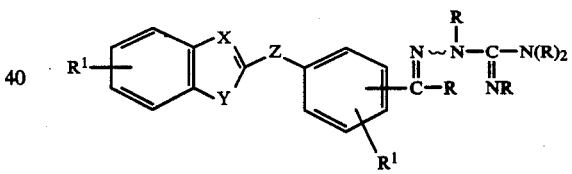

wherein $X$ is $-N-$ or $-\overset{R^2}{\underset{|}{C}}-$;

$Y$ is $-O-$, $-S-$, $-\overset{R^2}{\underset{|}{N}}-$, $-\overset{R^2}{\underset{|}{C}}=\overset{R^2}{\underset{|}{C}}-$, $-N=\overset{R^2}{\underset{|}{C}}-$ or $-\overset{R^2}{\underset{|}{C}}=N-$;

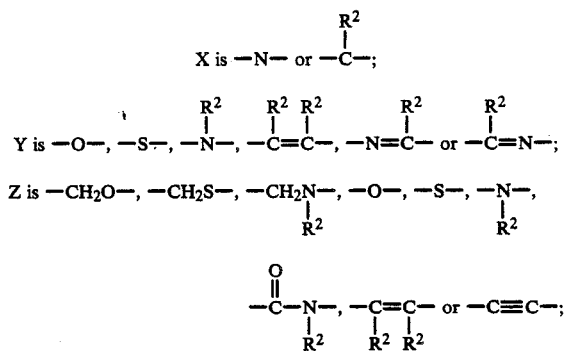

R is hydrogen, lower alkyl, phenyl or benzyl;

$R^1$ is hydrogen, lower alkyl, trifluoromethyl, amino, mono- or di-lower alkylamino, nitro, hydroxy, carboxy, lower alkoxycarbonyl, lower alkoxy or halo;

$R^2$ is hydrogen or lower alkyl; and the pharmaceutically acceptable salts thereof.

The terms "lower alkyl" and "lower alkoxy" refer to moieties having 1 to 6 carbon atoms in the carbon chain. The term "halo" refers to fluoro, chloro and bromo.

The compounds of the invention in which the bridge Z is —CH$_2$O— can be prepared by the reaction of an appropriate 3-hydroxyacetophenone with the halide of an appropriate benzo-fused heterocyclic derivative in the following representative sequence:

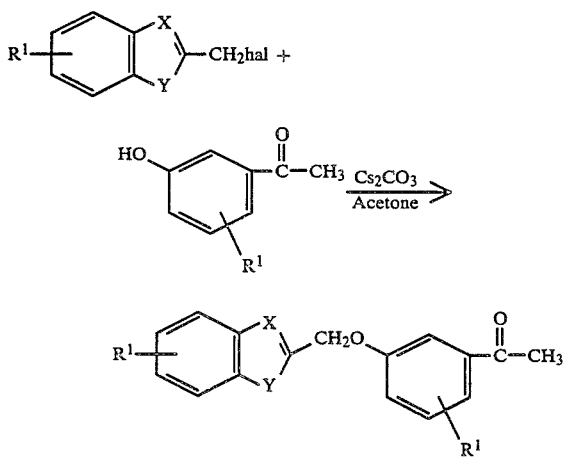

The intermediates obtained by this sequence are then further reacted to yield the desired aminoguanidine derivatives:

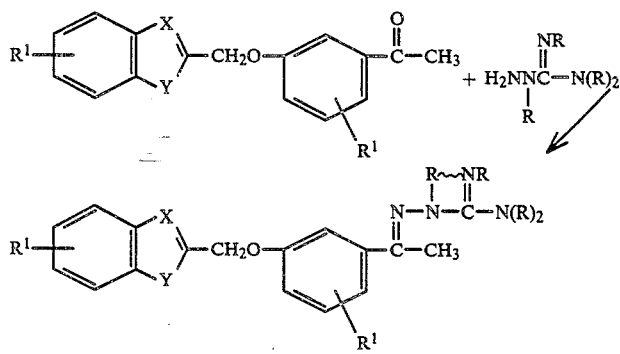

Compounds in which the bridge Z is —CH$_2$— and

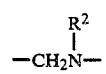

can be prepared in a like manner, starting with intermediates prepared by using the appropriate 3-mercaptoacetophenone or 3-aminoacetophenone derivative in place of the 3-hydroxyacetophenone derivative. Compounds in which the bridge Z is

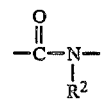

can be prepared by using the appropriate acyl chloride or acyl N-imidazole of the desired benzo-fused heterocyclic and an appropriately N-substituted alkoxyalkanoylacetophenone derivative.

The starting intermediate compounds for the preparation of compounds in which the linking bridge Z is

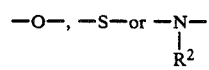

can be prepared by the following representative reaction sequence:

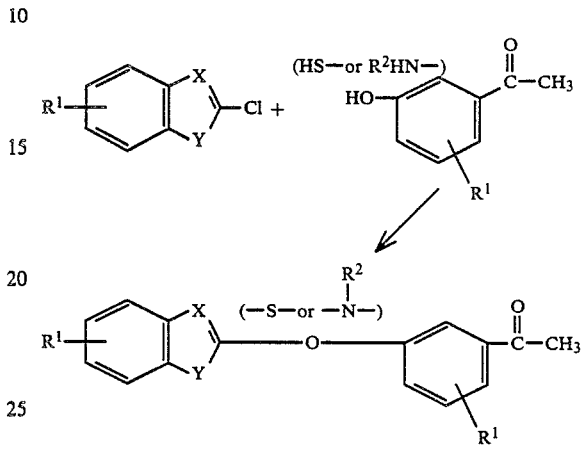

Other compounds within the scope of the invention can be prepared by similar conventional preparative methods using appropriate and readily available starting materials.

The benzo-fused heterocyclic compounds used in the above reaction sequences are either commercially available or can be prepared by methods conventional in the art. Thus, for example, such intermediates as 1-methyl-2-chloromethylbenzimidazole, 2-chloromethylbenzthiazole and 2-chloromethylbenzoxazole can be prepared by the following reaction scheme

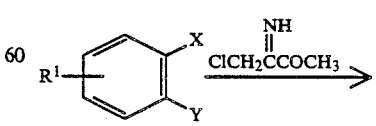

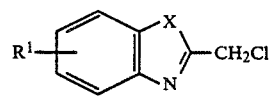

wherein X is O, S or NCH₃. The reaction is preferably carried out at a controlled low temperature in an organic solvent,, such as methylene chloride.

Compounds of the invention which contain a basic nitrogen are capable of forming pharmaceutically acceptable salts, including the salts of pharmaceutically acceptable organic and inorganic acids such as hydrochloric, hydrobromic, sulfuric, nitric, phosphoric, methanesulfonic, benzenesulfonic, acetic, citric, fumaric, maleic, succinic and the like.

The compounds of the invention, by virtue of the ability to inhibit the activity of lipoxygenase enzyme and cyclooxygenase enzyme, are useful in the treatment of inflammatory conditions. Accordingly, the compounds are indicated in the treatment of such diseases as rheumatoid arthritis, osteoarthritis, tendinitis, bursitis and similar conditions involving inflammation.

When the compounds of the invention are employed as antiinflammatory agents, they can be formulated into oral forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-distintegrating agents and the like may be employed. The compounds may be encapsulated with or without any carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase and cyclooxygenase inhibitory, and antiinflammatory effects of the compounds of the invention may be demonstrated by standard pharmacological procedures, which are described more fully in the examples given hereinafter.

These procedures illustrate the ability of the compounds of the invention to inhibit the polymorphonuclea leukocyte synthesis of the lipoxygenase oxidation product $LTB_4$; measure the ability of the compounds to inhibit the synthesis of the cyclooxygenase product $TxB_2$; measure the ability of the compounds to inhibit the synthesis of leukotriene and prostaglandin in the mouse macrophage assay; measure the in vivo activity of the compounds as lipoxygenase and cyclooxygenase inhibitors in the rat carageenan paw edema assay; and measure the ability of the compounds in the adjuvant arthritis assay.

The following examples show the preparation and pharmacological testing of compounds within the invention.

EXAMPLE 1

2-[1-[3-(2-Naphthalenylmethoxy)phenyl]ethylidene]-hydrazinecarboximidamide, 0.1 hydrate

A. 3-(2-Naphthalenylmethoxy)acetophenone

A mixture of 3-hydroxyacetophenone (19.2 g, 141 mmol), 2-chloromethylnaphthalene (25.0 g, 141 mmol), cesium carbonate (23 g), sodium carbonate (30 g), potassium iodide (0.5 g) and acetone (300 ml) is heated at reflux for 4 days. The reaction is filtered through a pad of Celite and silica gel. The solvent is removed in vacuo, giving a solid which is recrystallized from ethyl ether to yield 25.7 g of product (66% yield), m.p. 85°–87° C.

B.
2-[1-[3-(2-Naphthalenylmethoxy)phenyl]ethylidene]-hydrazinecarboximidamide The above product 2.26 g, 8.1 mmol) is combined with aminoguanidine bicarbonate (2.2 g, 16.2 mmol) in ethanol (100 ml) and refluxed overnight. The mixture is cooled to room temperature. A solid is filtered off, then recrystallized with ethyl acetate to give 1.47 g of product (55% yield), m.p. 176°–178° C.

Analysis for: $C_{20}H_{20}N_4O \cdot 0.1H_2O$ Calculated: C, 71.87; H, 6.09; N, 16.76 Found: C, 71.57; H, 5.87; N, 16.99.

EXAMPLE 2

2-[1-[3-(2-Quinolinylmethoxy)phenyl]ethylidene]hydrazinecarboximidamide

In a similar manner to Example 1A and using 2-chloromethylguinoline, 3-(2-quinolinylmethoxy)acetophenone is prepared (13.1 g, m.p. 57°–59° C., 47% yield). This product is reacted with amino guanidine bicarbonate as in 1B above to give 2.35 g of product (65% yield), m.p. 168°–170° C.

Analysis for: $C_{19}H_{19}N_5O$ Calculated: C, 68.44; H, 5.74; N, 21.00 Found: C, 68.04; H, 5.65; N, 21.21.

EXAMPLE 3

The compounds 5- and 12-hydroxyeicosatetraenoic acid (5-HETE and 12-HETE) and $LTB_4$ are early arachidonic acid oxidation products in the lipoxygenase cascade, which have been shown to mediate several aspects of inflammatory and allergic response. This is especially true with respect to 5,12-diHETE, which also denoted as $LTB_4$ [see Ford-Hitchinson, *J. Roy. Soc. Med.*, 74, 831 (1981)]. The assay of this Example measures the ability of the compounds of the invention to inhibit the synthesis of $LTB_4$ by rat glycogenelicited polymorphonuclear leukocytes (PMN).

The assay is carried out as follows:

Rat polymorphonuclear leukocytes (PMNs) are obtained from female Wistar rats (150–200 g) which receive an injection of 6% glycogen (10 ml i.p.). Rats are sacrificed 18–24 hours post injection by $CO_2$ asphyxiation and the elicited cells are harvested by peritoneal lavage using physiological saline (0.9% NaCl). The exudate is centrifuged at 400×g for 10 minutes. The supernatant fluid is discarded and the cell pellet is resuspended in a concentration of $2.0 \times 10^7$ cells/ml in HBSS containing $Ca^{++}$ and $Mg^{++}$ and 10 μM L-cyteine.

To 1 ml aliquots of cell suspension, test drugs or vehicle are added, then preincubated at 37° C. for 10 minutes. A23187 (1 μM) and [$^3$H]-AA (3.0 μCi/ml) are then added and the samples are further incubated for 10 minutes. The reaction is terminated by centrifugation and pelleting cells. Supernatants are then analyzed by HPLC analysis on a 15 cm×4.6 mm ID Supelcosil LC-18 (Supelco)(3M) column, using a two solvent system at a flow rate of 1.4 ml total flow as follows:

Solvent A: 70:30 17.4 mM $H_3PO_4$:$CH_3CN$
Solvent B: $CH_3CN$
Gradient: (system is equilibrated with Solvent A)

| Time | Percent A | Percent B |
|---|---|---|
| 0 | 100 | 0 |
| 15.0 | 100 | 0 |
| 20.0 | 65 | 35 |
| 40.0 | 65 | 35 |
| 42.0 | 10 | 90 |
| 50.0 | 10 | 90 |
| 50.1 | 100 | 0 |

Percent solvent changes are accomplished in a linear fashion.

Injections: 150 μl of each supernatant is injected directly onto column and $^3$H arachidonic acid metabolites are monitored using an on-line radioactivity detector (Ramona, IN/US, Fairfield, NJ).

Standards: $10^4$–$2.0 \times 10^4$ dpm of eicosanoids of interest are injected in 90 μl EtOH cocktail.

Co-chromatography with standard [$^3$H] leukotriene B$_4$ (LTB$_4$) in medium of stimulated PMN exposed to drug is compared to that found in medium of stimulated cells exposed to no drug, generating percent inhibition.

The compounds of this invention, when tested in this assay give results which are summarized in Table 1, where those compunds having an inhibition of >50% are designated by a "+". Other results are expressed as an IC$_{50}$ value.

TABLE 1

| Compound of Example Number | >50% Inhibitory at 50 μm | (IC$_{50}$) μm |
|---|---|---|
| 1 | | 8.9 |
| 2 | + | |

The results show that compounds of this invention have significant activity in inhibiting the synthesis of the arachidonic acid lipoxygenase oxidation product LTB$_4$.

EXAMPLE 4

The procedure of Example 3 is also employed for the determination of the extent to which compounds in the scope of the invention inhibit the synthesis of the arachidonic acid cyclooxygenase oxidation product TxB$_2$.

In this assay, the procedure of Example 3 is carried out as described. However, in order to determine cyclooxygenase activity, the samples are co-chromatographed with authenic reference [$^3$H]-TxB$_2$.

The results are calculated as in Example 3 and presented below:

TABLE 2

| Compound of Example No. | (IC$_{50}$) μm |
|---|---|
| 1 | 11.2 |

The results show that the compound tested has activity in inhibiting the synthesis of the arachidonic acid cyclooxygenase oxidation product TxB$_2$.

EXAMPLE 5

The ability of the compounds of the invention to inhibit both leukotriene and prostaglandin synthesis is examined in an assay which measures the ability of the compounds of the invention to inhibit the synthesis of PGE$_2$ and LTC$_4$ by murine peritoneal macrophages.

The assay is carried out as follows:

Macrophages are removed from the peritoneal cavity of 55–57 day old CD-1 mice (killed by CO$_2$ asphyxiation) by peritoneal lavage and centrifuged at 400×g for ten minutes. The cells are resuspended in Medium 199 and $4 \times 10^6$ cells are allowed to adhere on 35×10 mm Petri dishes for 1.5 hours at 37° C. in an atmosphere of 95% air and 5% CO$_2$. The cell monolayers are washed and incubated overnight in Medium 199 supplemented with 10% heat inactivated bovine serum containing 1 μCi[$^{14}$C]-arachidonic acid, or in the absence of $^{14}$C-arachidonic acid when the supernatant is to be assayed by radioimmunoassay (RIA). The labeled cells are then washed and incubated at 37° C. for 2 hours in Medium 199 with the prostaglandin stimuli, zymosan, or 12-o-tetradecanoyl-phorbol-13-acetate (TPA) and in the presence or absence of test compounds. Following incubation, the supernatant is removed and subjected to radioimmunoassay in order to determine the percent inhibition of prostaglandin E$_2$ and leukotriene C$_4$ by the test compounds. The results in the assay for compounds of the invention are presented in Table 3.

TABLE 3

| Compound of Example No. | IC$_{50}$ (μm) PGE$_2$ | LTC$_4$ |
|---|---|---|
| 1 | 43 | 33 |

The results show that the compound tested has a significant inhibitory effect on the synthesis of PGE$_2$ and LTC$_4$ by murine peritoneal macrophages.

EXAMPLE 6

The compounds of the invention are further tested in the rat carrageenan paw edema assay to determine their ability to inhibit the acute inflammatory response.

This assay is carried out as follows:

140–180 gm male Sprague-Dawley rats, in groups of 6 animals are injected subcutaneously in the right paw with 0.1 ml of 1% carrageenan at zero time. Mercury plethysmographic readings (ml) of the paw are made at zero time and 3 hours later. Test compounds are suspended or dissolved in 0.5% methylcellulose and given perorally 1 hour prior to carrageenan administration.

The increase in paw volume (edema in ml.) produced by the carrageenan is measured. Paw edema is calculated (3 hour volume minus zero time volume), and percent inhibition of edema is determined. Unpaired Student's t-test is used to determine statistical significance.

The activity of standard drugs in this assay is as follows:

| Drug | Oral ED$_{50}$ (95% C.L.) mg/kg |
|---|---|
| Indomethacin | 3.7 (0.6, 23.8) |
| Aspirin | 145.4 (33.1, 645.6) |

-continued

| Drug | Oral ED$_{50}$ (95% C.L.) mg/kg |
|---|---|
| Phenylbutazone | 26.2 (2.3, 291.0) |

When tested in this assay, the compounds of the invention gave the following results:

TABLE 4

| Compound of Example No. | % Inhibition (peroral) |
|---|---|
| 1 | 42 (at 50 mg/kg) |
| 2 | 43 (at 100 mg/kg) |

The results show that the compounds tested have activity in the rat carrageenan paw edema assay, evidencing an effect on the acute inflammatory response.

EXAMPLE 7

The adjuvant arthritis assay is used to measure the ability of the compounds to influence the progress of a chronic inflammatory condition.

This assay is carried out as follows:

Polyarthritis is induced in groups of 6–10 Sprague-Dawley rats weighing between 180–220 g by a subcutaneous injection into the right paw of a dessicated *Mycobacterium butyricum* or *tuberculosis* (0.5 mg/0.1 ml) suspended in light mineral oil. Test compounds are administered orally in 0.5% methylcellulose using a daily regimen (except for weekends). Both hind paw volumes (ml.) are measured by mercury plethysmograph on day 0 or at the time of injection of the complete adjuvant. Increases in paw volume (viz. edema) are determined for both paws on days 4 and 16. Statistical analysis of differences in paw edemas is performed by using the unpaired, Student's t-test.

The results are summarized in Table 5.

TABLE 5

| Compound of Example No. | Oral dose mg/kg | % Change of Right Paw Edema at Day 4 | % Change of Left Paw Edema at Day 16 |
|---|---|---|---|
| 1 | 30 | 50 | 31 |

The results show that the compound tested exhibits quite a significant effect on subchronic or establishing inflammation (right paw edema on day 4) and a significant effect on immunologically-induced inflammation (left paw edema on day 16).

What is claimed is:

1. A compound having the formula:

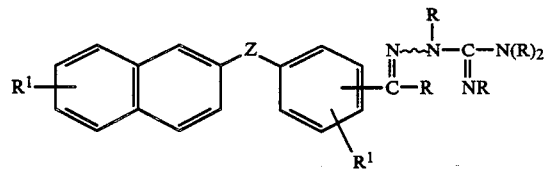

wherein

Z is $-CH_2O-$, $-CH_2S-$, $-CH_2N-$, $-O-$, $-S-$, $-N-$,
$\phantom{Z is -CH_2O-, -CH_2S-, -CH_2N-,\ }$ $|$ $\phantom{-O-, -S-,\ }$ $|$
$\phantom{Z is -CH_2O-, -CH_2S-, -CH_2N-,\ }$ $R^2$ $\phantom{-O-, -S-,\ }$ $R^2$

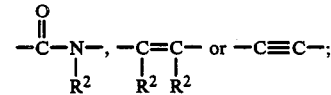

R is hydrogen, lower alkyl, phenyl or benzyl;
$R^1$ is hydrogen, lower alkyl, trifluoromethyl, amino, mono- or di-lower alkylamino, nitro, hydroxy, carboxy, lower alkoxycarbonyl, lower alkoxy or halo;
$R^2$ is hydrogen or lower alkyl;
and the pharmaceutically acceptable salts thereof.

2. The compound of claim 1, having the name 2-[1-[3-(2-naphthalenylmethoxy)phenyl]ethylidene]hydrazinecarboximidamide.

* * * * *